US006225283B1

(12) United States Patent
Hashizume

(10) Patent No.: US 6,225,283 B1
(45) Date of Patent: May 1, 2001

(54) REMEDIES FOR EATING DISTURBANCE

(75) Inventor: Kiyoshi Hashizume, Matsumoto (JP)

(73) Assignee: Sumitomo Pharmaceuticals Company, Limited, Osaka (JP)

(*) Notice: Subject to any disclaimer, the term of this patent is extended or adjusted under 35 U.S.C. 154(b) by 0 days.

(21) Appl. No.: 09/214,597

(22) PCT Filed: Jul. 2, 1997

(86) PCT No.: PCT/JP97/02283

§ 371 Date: Jan. 8, 1999

§ 102(e) Date: Jan. 8, 1999

(87) PCT Pub. No.: WO98/01152

PCT Pub. Date: Jan. 15, 1998

(30) Foreign Application Priority Data

Jul. 10, 1996 (JP) .................................................. 8-201248

(51) Int. Cl.⁷ .................................................. A61K 38/00
(52) U.S. Cl. .................................................. 514/2
(58) Field of Search .................................................. 514/2

(56) References Cited

FOREIGN PATENT DOCUMENTS 8-165250A   6/1996   (JP) .

OTHER PUBLICATIONS

CA 123:330385, Petersen et al., 1995.*
Eur. J. Endocrinol. vol. 136. 136, No. 5 (1997) pp. 445–460.
Clinical Endocrinology, vol. 25, No. 6 (1977) pp. 657–660 (Chemical Abstracts, vol. 87 (1977) Abstract No 82675).
Horm, Metab. Res., vol. 24, No. 6 (1992) pp. 297–299.

* cited by examiner

*Primary Examiner*—Kimberly Jordan
(74) *Attorney, Agent, or Firm*—Birch, Stewart, Kolasch & Birch, LLP

(57) ABSTRACT

This invention provides a therapeutic agent for the treatment of an abnormal eating behavior. The psychotic symptoms characteristic of anorexia nervosa such as apocleisis, intentional vomiting, eating in secret and the like have been treated with a tranquilizer and the like, but the effectiveness was only limited. By administration of a therapeutic agent according to the present invention, i.e., a human growth hormone (hGH) formulation, a will to eat can spontaneously be developed in a patient who previously received a nutrition only passively by means of a forcible nutrition program or a nasal nutrition supply. It is effective especially against the eating disorder in anorexia nervosa attributable possible to an increased central growth hormone releasing factor (GRH)-hGH secretion system.

6 Claims, 5 Drawing Sheets

Figure 1a

Appendix 2  Eating behavior surveillance table

Name_____  Male/Female
Age_____
Current body weight_____kg   stature_____cm
Maximum previous body weight_____kg ( Year,   Month)
Minimum previous adult body weight_____kg ( Year,   Month)

Answer to each question by marking a circle in the place which describes you best.

| | Always | Very Frequently | Frequently | Sometimes | Rarely | Never |
|---|---|---|---|---|---|---|
| 1. I'm afraid of gaining too much weight. | | | | | | |
| 2. I avoid eating even when I'm hungry. | | | | | | |
| 3. I think about nothing other than foods. | | | | | | |
| 4. I ever ate too much with thinking that I could not stop. | | | | | | |
| 5. I cut a food into small pieces. | | | | | | |
| 6. I'm conscious about the calorie of the food I eat. | | | | | | |
| 7. I avoid a food containing a large amount of carbohydrates (such as breads, potato, rice and the like) more intentionally. | | | | | | |
| 8. I think other people want me to eat more. | | | | | | |
| 9. I vomit after eating. | | | | | | |
| 10. I think after eating that I did a very wrong. | | | | | | |
| 11. I can't think any other thing than becoming more skinny. | | | | | | |

Figure 1b

12. I think the calories can be depleted by exercise.
13. Everyone thinks that I'm too skinny.
14. I'm obsessed by the thought that my body puts on fats.
15. It takes a longer time for me to eat than others.
16. I avoid a food containing sugar.
17. I eat a diet food (slimming food).
18. My life is confused by foods.
19. I'm under self control of foods.
20. I feel that I am forced by others to eat.
21. I waste my time for foods or think too much about foods.
22. I feel unpleasant after eating a sweet food.
23. I make every effort to be on a diet (restricted meals).
24. I like to feel my stomach empty.
25. I don't want to try a new nutritional food product.
26. I have an urge to vomit after eating.

Menstruation (circle a number if you are a woman)

1) Never

2) Regular (25 to 38-day cycle with a deviation of the period within a week)

3) Irregular

4) Previously usual but currently complete amenorrhea

5) Once amenorrhea for three months or longer but thereafter re-menstruated

Figure 1c

Criteria for judgment of eating behavior surveillance table

1. Body weight

A standard body weight for the stature is obtained (see Appendix 3, 4 and 5).

The previous minimum adult weight lower than a standard body weight by 20 % or more is required to judge "morbid emaciation ⊕ ".

2. Scores to 26 questions for eating behavior

The score is 3 for the answer "Always", 2 for "Very Frequently", and 1 for "Frequently". A total score of 20 or higher is required to judge "abnormal eating behavior ⊕ ".

3. Menstruation

When 1), 4) or 5) is circled, the judgment is "amenorrhea ⊕ ".

When these three items are all positive, then eating disorder is highly suspected.

REMEDIES FOR EATING DISTURBANCE

This application is the national phase under 35 U.S.C. §371 of prior PCT International Application No. PCT/JP97/02283 which has an International filing date of Jul. 02, 1997 which designated the United States of America.

TECHNICAL FIELD

The present invention relates to a therapeutic agent for the treatment of a psychotic symptom accompanying anorexia nervosa. More particularly, the present invention relates to a therapeutic agent for the treatment of an abnormal eating behavior in anorexia nervosa attributable to an abnormally increased central GRH level.

PRIOR ART

Anorexia nervosa (or nervous asitia, apocleisis) is a disease exhibiting psychotic symptoms such as a characteristic desire for emaciation and an abnormal eating behavior as well as somatic symptoms such as an extreme leptosome observed as a weight loss by 20% or more of the standard body weight as well as amenorrhea, and develops frequently in juvenile women. It is diagnosed generally based on the following clinical findings.

A: Abnormal weight loss by 20% or more of standard body weight
B: Abnormal eating behavior (apocleisis, vomiting, eating in secret, hyperphagia and the like)
C: Obsessed recognition with regard to body weight or body shape
D: Onset age of 30 years old or younger
E: Amenorrhea (in women)
F: Absence of organic disease causative of emaciation (such as schizophrenia and depression)

It is a serious, sometimes fatal disease with no insight in a patient.

In a current treatment, a less potent psychotropic agent or an antianxiety agent is administered depending on the symptoms and an oral tube feeding diet or a high calorie drip infusion is employed for recovery from an extreme physical exhaustion (See, "Today's treatment guideline", IGAKUSHOIN (1995 Ed.), p248). However, no essential therapeutic agents capable of removing the psychotic symptoms characteristic of anorexia nervosa and also capable of normalizing the eating behavior have been reported.

On the other hand, human growth hormone (hereinafter abbreviated as hGH) is employed in the treatment of pituitary dwarfism and is believed to be effective also in the promotion of the healing of fractures and burn wounds and in the treatment of a patient having a reduced absorption of nutrition ("NIKKEI BIONENKAN" 94/95). Nevertheless, except for the improvement and exaltation in feeling associated with the recovery from a physical exhaustion state, no effectiveness of hGH against the typical psychotic symptoms has not been suggested.

Recently, a patent disclosed that administration of hGH is useful against various diseases caused by the reduction in triiodothyronine (T3) which is a thyroid hormone (WO95/24919). The inventors mentioned anorexia nervosa as an example of disease of T3 reduction syndrome, but all clinical effects of hGH they observed were an hGH-induced improvement in insufficient nutrition absorption only in the peripheral tissues after a trauma or an organ implantation, and all of their data (increased blood IGF-I level and reduced urinary nitrogen) can be interpreted based on the known peripheral effects of hGH.

SUMMARY OF THE INVENTION

An objective of the present invention is to provide a therapeutic agent for the treatment of the psychotic symptoms of anorexia nervosa which may be a core of this disease. As a result, a patient having anorexia nervosa which is difficult to treat and which imposes a substantial load on the family and the physicians can satisfactorily be treated.

We focused on the findings that in anorexia nervosa the level of IGF-I (insulin-like growth factor-I) is low in spite of the exhaustion state exhibiting an increased blood hGH level, and then the extensive studies resulted in an understanding that in this disease the central GRH level is elevated and it triggers the psychotic symptoms. Then we administered hGH to a typical anorexia nervosa patient, and observed a psychotic symptom improving effect in addition to a peripheral nutriture recovering effect, whereby establishing the present invention. These effects may be due to the negative feedback to the central GRH secretion by an exogeneous hGH.

Thus, the present invention relates to the following pharmaceuticals:

(1) A therapeutic agent for the treatment of a psychotic symptom accompanying anorexia nervosa comprising a human growth hormone as an active ingredient.
(2) A therapeutic agent according to item (1) wherein said psychotic symptom accompanying anorexia nervosa is abnormal eating behavior.
(3) A therapeutic agent according to item 1 or 2 wherein the anorexia nervosa is accompanied by abnormality in biochemical parameters of A or B given below:
A: Increased level of central growth hormone releasing factor (GRH)
B: Reduced blood IGF-I response to increased growth hormone (hGH)

BRIEF DESCRIPTION OF THE DRAWINGS

FIG. 1 shows a eating behavior surveillance table and a criteria for judgment made by the anorexia nervosa survey and study group of Ministry of Health and Welfare.

DETAILED DESCRIPTION OF THE INVENTION

Figure 2:
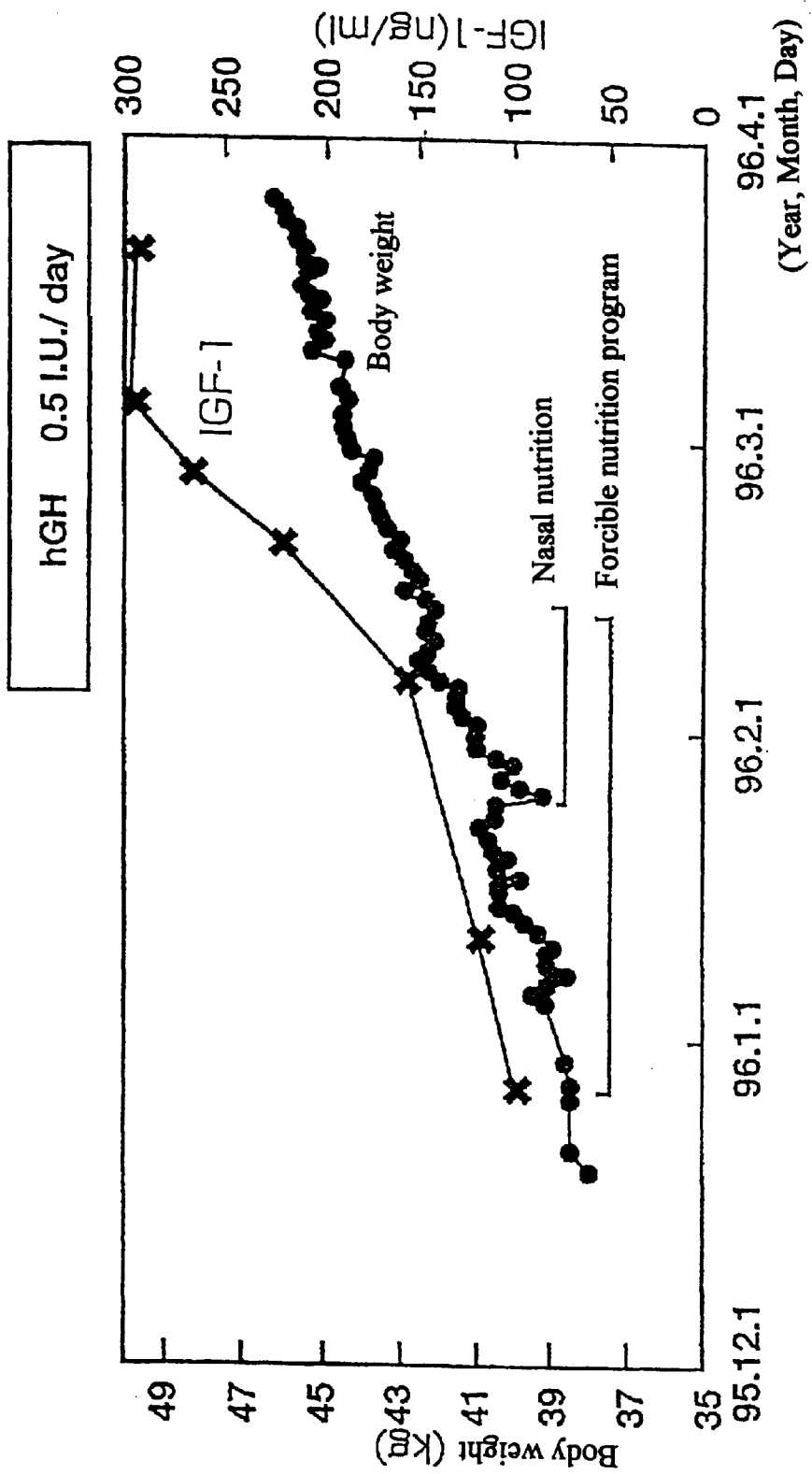
FIG. 2 shows the change in the condition in Case No. 1 before and after administration of hGH. The graph plotted with [×] shows the blood IGF-I levels, while the graph plotted with [●] shows the body weights.

The present invention is described below.

Human growth hormone (hGH) has practically been used for about 20 years as a therapeutic agent for the treatment of pituitary dwarfism and various pharmaceutical formulations are marketed currently.

In the present invention, any pharmaceutical formulation having an hGH activity may be employed. In view of the problems of the antigenicity, a mature hGH is preferred. Nevertheless, a purified product derived from a natural pituitary gland, Met-hGH having a methionine residue at the N-terminal, and a recombinant hGH variant may also be encompassed in the present invention as far as they are the pharmaceutical formulations having hGH activities.

While the formulation may be a liquid formulation or a lyophilized formulation, a subcutaneous formulation is particularly preferred. Each of these parenteral formulations may contain a stabilizer and a carrier known in the art, and is used preferably as an isotonic solution. The carrier may be a plasma-derived protein such as albumin, an amino acid such as glycine, a saccharide such as mannitol. Preferable examples are found in Japanese Patent Application Kohyo No. 503764/1991. Generally, a lyophilized formulation for subcutaneous or intramuscular administration is employed, and the representative formulation is GENOTROPIN 16 IU (Pharmacia Upjohn) for injection.

In the present invention, the expression "psychotic symptoms accompanying anorexia nervosa" means an abnormal concern or desire with regard to eating and resultant abnormal eating behavior (apocleisis, vomiting, eating in secret, hyperphagia). While concrete criteria employed in the diagnosis may vary depending on the findings by medical specialists, a standard is shown in FIG. 1 which shows a eating behavior surveillance table and a criteria for judgment made by the specified diseases/anorexia nervosa survey and study group of Ministry of Health and Welfare.

In the present invention, the expression "abnormal biochemical parameters" means that the level of an endogeneous hormone or a neurotransmitter is different significantly from a standard level in healthy humans or from the level observed in an patient when the identical patient was in a normal condition.

The expression "a high central growth hormone release factor (GRH) level" means a hypersecretion of GRH or hGH in the central nerve/hypothalamus or in the pituitary gland, which is identified usually by a plasma GRH level determined by a radioimmunoassay or an enzyme immunoassay not less than 30 pg/ml which is the upper limit of the normal range (3 to 30 pg/ml) [Clin. Chim. Acta; Vol. 202, p243–254 (1991) and Clin. Chem. Enzym. Communs.; Vol. 4, p305–310 (1992)]. An indirect assumption may be made based on an hGH level in a peripheral blood not less than 10 ng/ml in the absence of organic causative diseases such as hGH-producing tumor.

The expression "a reduced blood IGF-I response to an increased growth hormone (hGH)" means a condition in which the blood IGF-I level is not elevated in spite of a higher blood hGH level, i.e., not less than 10 ng/ml which is the upper limit of the normal range. Typically, a condition in which the blood IGF-I level is 200 ng/ml or less and below the level higher by 20 times than the blood hGH level is applicable. Since in such condition no negative feedback by IGF-I occurs, the GRH production in the hypothalamus is increased abnormally, resulting in an abnormality in the appetite center, which may lead to the abnormal eating behavior.

While hGH may be administered subcutaneously, intravenously or intramuscularly, it is usually administered subcutaneously. The dose and the frequency of the administration of hGH may vary depending on the condition, the age and the sex of a patient, etc. and one session generally comprises 0.05 to 5 units/day for 3 months, especially 0.2 to 1 unit/day for 1 week or longer.

As described above, a hGH-containing formulation according to the present invention is capable of improving the psychotic symptoms, particularly the abnormal eating behavior based on the central abnormality, in a patient having anorexia nervosa. It enables a novel therapy in a clinical practice currently having no particular effective pharmaceuticals.

EXAMPLES

The present invention is further described in the following examples.

Example 1

Case No. 1 Pretreatment findings

The patient was a 17 years old woman having diagnosed anorexia nervosa accompanied with the major symptoms such as weight loss, fatigue and amenorrhea. The body weight and the stature at the initiation of the treatment was 37.8 kg and 156.0 cm (BMI:15.5).

The biochemical parameters of endocrinal function were as follows.

[Thyroid functions] T3: Low level (78.5 ng/dl), T4: Low level (6.8 g g/dl), TBG: Low level (18.1 μg/ml), TRH test: Retarded response, Blood TSH levels (1.9, 13.5, 20.7, 24.5 and 27.5 μIU/ml) after TRH loading (0, 30, 60, 90 and 120 minutes).

[Growth hormone secretion functions] GRH test: Normal response, 1-DOPA test: Low response (See Table 1).

TABLE 1

| | GH secretion (ng/ml) | |
|---|---|---|
| Time after loading | GRH | 1-DOPA |
| 0 | 15.2 | 2.9 |
| 15 | 69.2 | — |
| 30 | 51.6 | 2.9 |
| 60 | 40.5 | 6.1 |
| 90 | 14.9 | 2.2 |
| 120 minutes | 2.8 | 3.6 |

[IGF-I secretion function] IGF-I: 40.4 (GH: 5.9 ng/ml), IGF-I:39.8 (GH: 5.9 ng/ml). The blood samples determined twice exhibited an IGF-I level which was particularly lower relative to the GH level.

Case No. 1, Treatment

Figure 3:
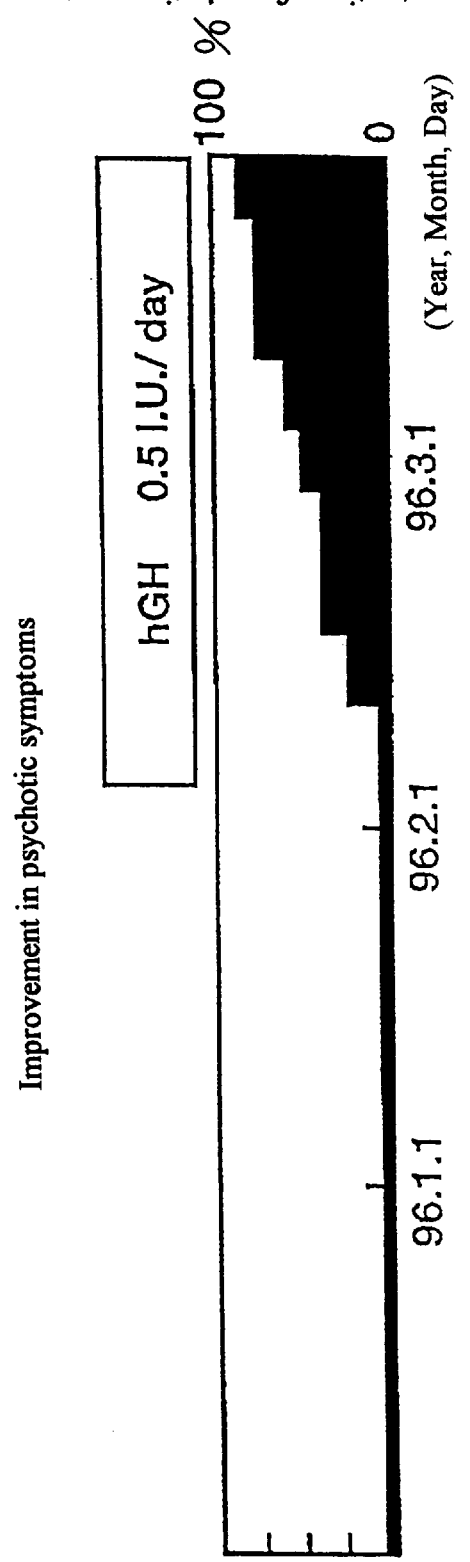
FIG. 3 shows the change in the condition in Case No. 1 before and after administration of hGH. The histogram shows the general improvement ratings of the psychotic symptoms of anorexia nervosa/abnormal eating behavior based on the findings by a physician. The % values on the ordinate represent the improvement ratings of the eating behavior, with 0% representing an extremely abnormal eating behavior (score of 26 or higher in the table in FIG. 1) and 100% representing a completely normal behavior.

As shown in FIG. 2, a forcible nutrition program for about 50 days after admission (December, 1995) resulted in no satisfactory weight gain or improvement in the eating behavior. Accordingly, for the purpose of recovering the physical strength, a nasal nutrition supply was initiated at the 30th day, and after 20 days no spontaneous eating was observed and no improvement in the psychotic symptoms were observed, although the body weight and the IGF-I level were increased slightly. Administration of 0.5 IU/day of a recombinant hGH formulation (GENOTROPIN for injection (Pharmacia/Upjohn)) initiated on the 40th day resulted in a rapid weight gain and an increase in the IGF-I level as well as a spontaneous eating which began 2 days after initiation of the administration, exhibiting a marked improvement in the eating behavior. On the 30th day of the hGH treatment, the body weight was 45.0 kg and the IGF-I level was 300 ng/ml, indicating the recovery of the normal levels. The psychotic symptoms/eating disorder was considered to be removed, and she now receives continuous hGH treatment (May, 1996) and shows no psychotic symptoms of anorexia nervosa/eating disorder. FIG. 2 and FIG. 3 show the conditions before and after hGH treatment.

After 1 year of the growth hormone treatment, the patient showed the score of 8 in total for the 26 questions in the eating behavior surveillance table shown FIG. 1 (a score of 20 or higher is required for the abnormal eating behavior in this criteria). In view of the score before the growth hormone treatment which was 26 as well as a typical image of anorexia nervosa observed previously, the growth hormone treatment is considered to be extremely useful for improving the psychotic symptoms/eating disorder associated with anorexia nervosa.

Example 2

Case No. 2, Treatment

The patient was an 18 years old woman (body weight: 36.6 kg, stature: 160 cm). The total score was 23 before the growth hormone treatment, but reduced to 16 after the treatment with 1 IU of a recombinant hGH formulation (GENOTROPIN for injection (Pharmacia/Upjohn)) once a day continuously for 2 weeks.

Example 3

Case No. 3, Treatment

The patient was a 23 years old woman (body weight: 32 kg, stature: 154 cm). The abnormal eating behavior score was 30 before the growth hormone treatment, but reduced to 25 after the treatment with 1 IU of a recombinant hGH formulation (GENOTROPIN for injection (Pharmacia/Upjohn)) once a day continuously for 2 weeks.

What is claimed is:

1. A method for treating anorexia nervosa which comprises administering to a patient in need thereof an effective amount of human growth hormone.

2. The method according to claim 1, wherein administering the human growth hormone is performed intravenously.

3. The method according to claim 1, wherein administering the human growth hormone is performed intramuscularly.

4. The method according to claim 1, wherein administering the human growth hormone is performed subcutaneously.

5. The method according to claim 1, further comprising administering the human growth hormone in a session which comprises 0.05 to 5 units/day of human growth hormone for three months.

6. The method according to claim 1, further comprising administering the human growth hormone in a session which comprises 0.2 to 1 unit/day of human growth hormone for at least one week.

\* \* \* \* \*